United States Patent [19]

Gabbay

[11] Patent Number: 4,491,986
[45] Date of Patent: Jan. 8, 1985

[54] HEART VALVE

[76] Inventor: Shlomo Gabbay, 1740 Bogart St., Bronx, N.Y. 10462

[21] Appl. No.: 841,791

[22] Filed: Oct. 13, 1977

Related U.S. Application Data

[63] Continuation-in-part of Ser. No. 685,543, May 12, 1976, abandoned, which is a continuation-in-part of Ser. No. 609,685, Sep. 2, 1975, abandoned, which is a continuation-in-part of Ser. No. 533,989, Dec. 18, 1974, abandoned.

[51] Int. Cl.³ .................................................. A61F 1/22
[52] U.S. Cl. .......................................................... 3/1.5
[58] Field of Search ......................................... 3/1.5, 1

[56] References Cited

U.S. PATENT DOCUMENTS 3,445,916  5/1969  Schulte ...................................... 3/1.5
3,739,402  6/1973  Cooley et al. ............................ 3/1.5

OTHER PUBLICATIONS

"Heart Valve Replacement with Autologous Fascia Lata", by M. I. Ionescu et al., The Journal of Thoracic & Cardiovascular Surgery, vol. 60, No. 3, Sep. 1970, pp. 331-354.

*Primary Examiner*—Ronald L. Frinks

[57] ABSTRACT

A prosthetic heart valve including a supporting structure comprising a substantially semi-circular base or armature of semi-rigid but somewhat flexible material with two upwardly projecting struts. The armature and struts may be encased with plastic or other suitable material; and are covered with soft flexible material including a strip which connects the free ends of the semi-circular base to form a complete ring. A membrane of biological or biologically acceptable material is shaped about the supporting structure so as to define a cylindrical orifice having lips which overlap, over a significant part of their inside surfaces, to provide a complete and effective closure against and under the force of back-flow. When said lips open the flow is relatively unobstructed. The soft strip of material which completes the armature ring permits the valve to respond more readily to movements of the heart while the semi-rigid section provides adequate support for the valve. The armature and struts may be formed to either a semi-oval or, preferably, semi-circular configuration and made from wire, metal strip, or plastic, or a combination of metal and plastic, all depending upon the application. The struts may be of equal height or different heights. If required the base may be formed completely from metal or plastic.

9 Claims, 31 Drawing Figures

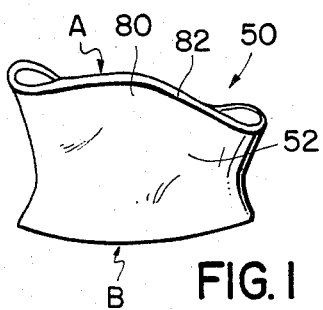
FIG. 1
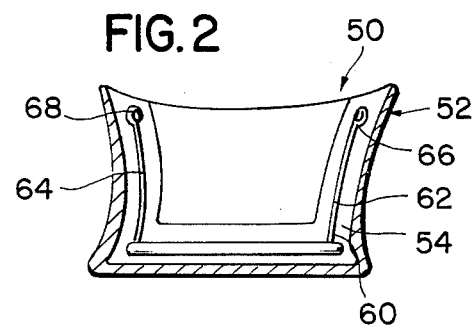
FIG. 2
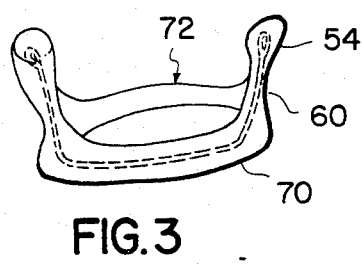
FIG. 3
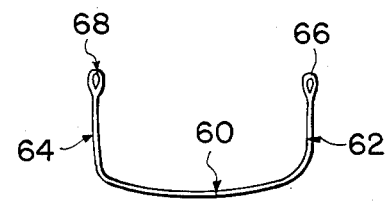
FIG. 4
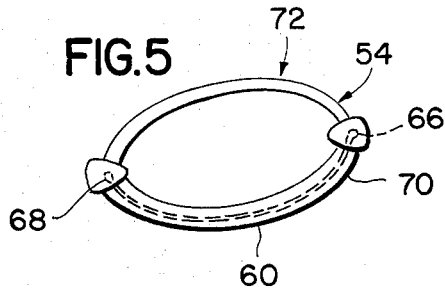
FIG. 5
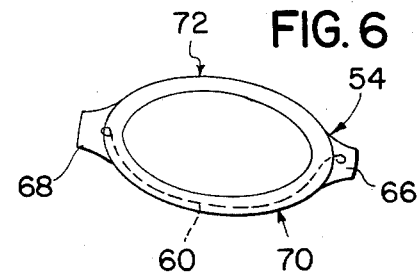
FIG. 6
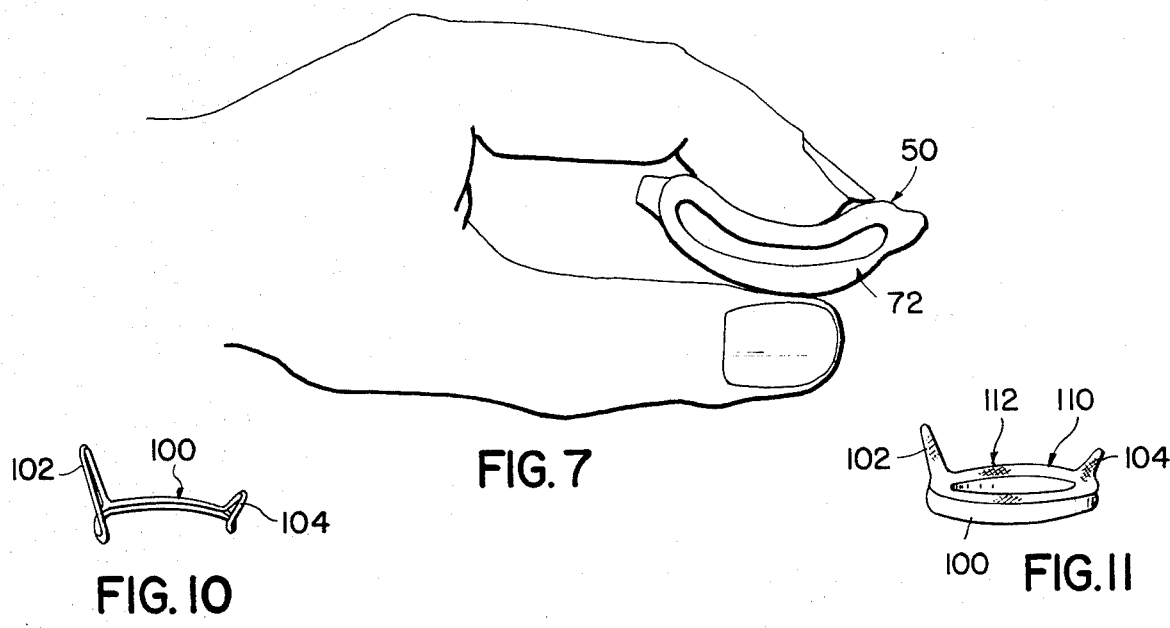
FIG. 7
FIG. 10
FIG. 11

HEART VALVE

CROSS REFERENCE

This application is a continuation-in-part of my U.S. application Ser. No. 685,543 filed 05/12/76, in which in turn is a continuation-in-part of my U.S. application Ser. No. 609,685 filed 09/02/75, which in turn is a continuation-in-part of my application Ser. No. 533,989 filed 12/18/74, all abandoned.

BACKGROUND OF THE INVENTION

1. Field of Application

This invention relates to valves for the human heart and more particularly to a prosthetic heart valve.

2. Description of the Prior Art

In the field of heart valves there have been many attempts to produce a valve that is similar or substantially similar to the natural heart valve. The reason for this is that if the replacement valve differs in any substantial way from the natural valve its reaction in the heart muscle might be so detrimental as to cause failure of the heart itself. One of the most commonly used valves is known as the Starr-Edwards valve. It includes a circular ring with three vertical struts which project upwardly therefrom and join together to form a cage. A steel or plastic ball having a larger diameter than the opening in the ring is movably entrapped in the cage. The pressure of blood flowing through the ring will move the ball away from the ring and permit blood flow through the valve. The reversal of pressure will cause the ball to be seated once again against the ring and thereby block flow through the valve.

There are many problems with the Starr-Edwards type valve. Firstly, the flow is not axial since it must flow around the ball. Such a flow quite often creates a very serious problem since it tends to cause turbulence (eddy currents) which restrict the flow of blood and may cause blood clots. The presence of blood clots in turn leads to thromboembolisms and to prevent this substantial amounts of anticoagulants must be used.

Such blood clots also tend to form around the circular ring and prevent the ball from properly seating itself to close the valve. This leads to serious leakage and ultimate death to the person having the valve. The energy lost in moving the ball is a substantial strain on the heart; and the ball, when it seats against the ring, tends to crush blood cells. Also the cage member, when it projects into the heart causes an obstruction that tends to scar the opposing wall of the heart during the pumping motion. Moreover the ball will occasionally become entrapped in the open position in the cage because of the blood clots or it may escape entirely from the cage. Finally, there is a constant clicking sound caused by the ball hitting the ring, which tends to disturb the person having the valve. These problems have been substantial and have lead to the death of many persons who have had this type of artificial heart valve.

There has been some work done in attempting to produce a valve which simulates the shape and axial flow characteristics of the natural heart valve, and of course, eliminate the ball. Most of these have been directed to tricuspid or three-lip valves.

One such valve requires the use of certain heart valves from swine. One of the problems with this is that hundreds of pigs have to be slaughtered before one or two perfect valves can be found. Secondly, since it is a tricuspid valve, as will be explained hereinafter, if there is slight damage or shrinkage to one of the cusps the valve will not properly close. Also swine valves are not particularly large and because of mounting problems only about 30% of the area of the ring can be used for the opening in the valve. Thus, much of the internal diameter of the normal heart valve is lost in the use of these valves.

Moreover, tricuspid valves have an inherent problem, in that the three lips must close in exact alignment or the valve will not be properly closed. If one lip is slightly out of line or mis-shapen the other two lips cannot make up for the difference and, therefore, leakage will occur. Likewise, after the valve has been used for a period of time, if one of the cusps becomes slightly inflexible or immobile, tissue will build up on that cusp to further reduce it mobility and thereby result in stenosis or total lack of movement of the cusp. This reduces the size of the opening and thereby the amount of blood flowing through the valve; it can cause turbulence in the flow blood and to improper closure. Failure of the valve will thereafter almost invariably occur. Also these valves can function only with rigid metal rings. These rings damage the heart by pressing on the tissues and creating arythmias. Another serious problem of the rigid ring is a high incidence of perivalvular leaks, because the openings in the natural heart valves normally move and they cannot once a rigid ring is inserted. These artificial heart valves thus have substantial problems. Some more of the problems are discussed in detail in the Journal of Thoracic and Cardiovascular Surgery Vol. 68, No. 3, September, 1974, pages 261 to 269.

There has been some effort to produce a two cusp valve which attempts to simulate the shape and flow of the natural heart valve. However, the principal problems with such a valve (as shown in U.S. Pat. No. 3,739,402) have been the lack of an adequate volume of blood flow through the valve and the inability to obtain complete closure. These problems are caused by the rigidity and inflexibility of the lips and also as aforementioned by a rigid supporting ring. The inflexibility of the lips is caused by the rigid ring and also by the tautness of the membrane, which forms the lips. As a result insufficient amount of blood will flow through the heart and cause a tremendous back pressure that can cause serious damage. Also the restriction on flow can cause clots and other serious side effects. Thus, a flexible ring is most important since flexibility will make the ring conform more closely to the overall movement of the heart muscle and will reduce arythmias and trauma to the heart and permit the heart to contract and expand in a manner more closely to normal.

In the patent it states that the lips can open only to approximately 2 millimeters. If we assume the total diameter of the main ring of the valve has to be about 3 centimeters in diameter (which is about the usual diameter of the valves in the human heart) the overall area of opening would be a slit which was 2 millimeters by 3 centimeters or 0.6 sq. cm. in area. When this is compared to the total area of the opening of the ring, which is $(3/2^2)$ about 7 sq. cm., it becomes apparent that the valve opens only to a small fraction of its total area, about 20%. Thus, only 20% of the amount of blood entering the valve will be able to leave resulting in a tremendous strain on the heart and valve, possibly leading to failure of both. Reduction in flow also caused tremendous back pressure within the heart, which can seriously damage the inside of the heart, and further, the restriction in flow can cause clots and other deleterious side effects. The restriction in flow is also complicated by the narrow shape of the struts. The membrane conforms to this narrow shape so that a narrow channel is formed throughout the valve. It is, therefore, seen that the valve not only has a narrow exit, but has a substantially reduced flow area throughout.

The inflexibility of the lips of the device of said patent cause them to close along a thin narrow line along their leading edge. This closing has two serious problems. By having such a narrow line of closure, the slightest deformity in either lip will prevent complete closing and cause leakage through the valve. Second, since the valve closes only along this narrow line, the valve is often unable to remain closed when subjected to the extreme pressures in the heart. This is especially important when the valve is used in the mitral position in the heart, since the pressure differential across the valve in that position is substantial, and any leakage could lead to cardiac failure.

The flexibility of the ring in certain positions, such as the aortic or mitral valve position, will reduce arythimias and trauma to the heart and cause it to function in a normal manner, since it will contract and expand with the heart muscle.

A heart valve is needed which closely simulates the natural heart valve by having the flexibility to open to substantially the same size as the natural opening and the flexibility to completely close and to remain closed against the force of large pressure differentials.

SUMMARY OF THE INVENTION

It is therefore an object of this invention to provide a prosthetic heart valve which closely resembles the natural heart valve.

It is a further object of this invention to provide a heart valve having axial flow, with two lips or cusps.

A still further object of this invention is to provide a heart valve where the lips have sufficient flexibility to open to the full diameter of the valve, and to fully close and remain completely closed.

It is still a further object of this invention to provide a heart valve where the supporting ring is flexible to permit the heart valve to move in co-ordination with movements of the heart.

Another object of this invention is to provide a heart valve which moves in conjunction with the annulus of the opening in which it is placed.

Another object of this invention is to provide a heart valve with a supporting ring which is partially constructed of flexible material.

Another object of this invention is to provide a heart valve where half of the supporting ring is partially inflexible and semi-rigid and half is non-rigid and very flexible.

Still another object of this invention is to provide a heart valve which is strong enough to resist the pressure of the heart without failure.

Yet still another object of this invention is to provide a heart valve having proper closure and minimal resistance to flow.

Yet still a further object of this invention is to provide a heart valve which is usable for the aortic valve.

Yet still another object of this invention is to provide a heart valve having no significant projections which will scar the inner lining of the heart.

Yet still another object of this invention is to provide heart valves having a base member that can either be a full or partial enclosure.

This invention involves prosthetic heart valves; and contemplates providing a support structure upon which a biologically acceptable membrane material may be secured in such a way as to define a cylindrical orfice terminating in relatively thin flexible lips that can come together over a significant portion of their inner surfaces. The support structure is formed upon a substantially semi-circular base of semi-flexible, semi-rigid material having a pair of upstanding struts and which is encased in, or otherwise covered by, soft flexible material that also provides a flexible band or strip to complete the semi-circular base forming same into a substantially circular base ring. The membrane is further responsive to back pressure on its outer surfaces, back from the opening, to force the lips together along the opening and substantially back therefrom, to prevent flow through the valve.

Other object, features, and advantages of the invention in its details of construction and arrangement of parts, will be seen from above, from the following description of the preferred embodiments when considered in conjunction with the drawings, and from the appended claims.

BRIEF DESCRIPTION OF THE DRAWINGS

FIG. 1 illustrates a heart valve incorporating the instant invention;

FIG. 2 is a cross-sectional view of the valve of FIG. 1;

FIG. 3 illustrates the support for the valve of FIG. 1;

FIG. 4 illustrates the armature and struts for the support as shown in FIG. 2;

FIG. 5 is a top view of the support of FIG. 2;

FIG. 6 is a bottom view of the support of FIG. 3;

FIG. 7 shows the valve of FIGS. 1-6 being flexed by a human hand before surgically being inserted into the heart;

FIG. 10 shows another alternative armature and struts construction;

FIG. 11 shows the armature and struts of FIG. 10, covered with material to form another alternative support;

DESCRIPTION OF THE PREFERRED EMBODIMENTS

Figure 8:
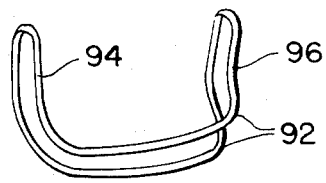
FIG. 8 shows an alternative armature and struts construction.

With reference to FIGS. 1 and 2, there is generally shown at 50 a prosthetic heart valve fabricated by forming a thin membrane 52 of biological material into the valve configuration, as will be hereinafter described, and securing membrane 52 to a valve support 54 (FIG. 2,3,5 and 6).

Prosthetic heart valve 50 is intended to replace one of the valves in the human heart, particularly the mitral, the aortic and/or the tricuspid. The size and configuration of valve 50 will thus depend upon the particular size and configuration of the human heart in which valve 50 is to be used and of the valve it is to replace. Valve 50 may be substantially circular, oval, or of a general roundish configuration.

Support 54 is built upon an armature or base 60 (FIGS. 2-4) formed from wire or suitable stock and having a pair of upstanding struts 62, 64 each terminating at an end 66, 68 respectively which may be rounded, folded over or otherwise formed so as to present a smooth and not a sharp end. Base 60 and struts 62, 64 are formed from a suitable strong material such as high grade surgical steel such as "Elgiloy". It should be a material that is not only strong but which also has flexibility. Struts 62, 64 are disposed to project slightly outwardly and are inclined at an angle of about 20 to 30 degrees. In some applications one of the struts 62, 64 may be longer then the other. Base 60 and struts 62,64 are preferably covered with plastic; such as medical grade silicone.

It is important to note that base 60 forms an incomplete or open configuration which may be either substantially semi-circular or substantially a semi-oval depending upon its end use.

A thin fabric 70, such as Dacron, which is biologically inert and flexible is thereafter applied over base 60 and struts 62, 64 to complete support 54. Again it is important to note that upon such completion of support 54 that the heretofore incomplete open circle formed by base 60 becomes a complete base ring 72 of either substantially circular or substantially ovular configuration.

Membrane 52 is thereafter applied to support 54, as by sewing (not shown) to the Dacron fabric 70 to cover support 54 and to form the configuration of valve 50. This membrane is made of a biological material such as dura mater (the membrane surrounding the human brain). The dura mater is taken from cadavers and processed so that it is totally inert and thus will not be subject to rejection by the human body. This material is extremely strong and flexible and has a high modulus of elasticity so that the valve can be continuously opened and closed with the membrane still retaining its original configuration. Other biologically acceptable materials are animal Pericardi treated with gluteraldehyde and dura mater of animals such as pigs and sheep, and calfs also treated by gluteraldehyde. Gluteraldehyde is used because the cross linking bonds increase the strength of the dura mater. Also gluteraldehyde is antiseptic and will sterilize the material before use.

Membrane 52 extends as shown in FIG. 1, so that it forms lips 80, 82 with edges that overlap to some extent since the membrane is applied to be loose and not taut, the length of the overlap being preferably about 20% of the distance between the exit end and the base of the valve. Because lips 80, 82 are loose and because of the diverging struts 60, 62, valve 50 will open so that the areas of the opening on the exit side "A" of valve 50 and on the entrance side "B" of the valve 50 are substantially the same. Blood will then readily flow through valve 50 without any significant loss of pressure. As such there is no substantial impediment and a minimal amount of friction to the passage of blood through valve 50. The exit opening being no larger than the entrance opening is in contrast to the prior art valve where the area of exit was less than the entrance and therefore, because of the venturi effect there was a substantial amount of frictional resistance to the flow of blood, and a substantial drop in said flow. This would put pressure on the heart and eventually lead to its failure. In the present valve that pressure differential is substantially eliminated. Pressure differential vs. Flow graphs comparing a heart valve constructed as described with some constructed in accordance with prior art teachings are described later in this description and more then adequately illustrate the superiority of the present invention.

Referring again to operation of valve 50, when the flow of blood reverses, the component of flow in both the vertical direction and in the horizontal direction on each side of loose lips 80, 82 will cause them to close. It will be appreciated that because of their loose construction and overlapping they will readily close, and when closed there will be no leakage. Also because of this looseness if one lip 80 or 82 is slightly rigid, such as when stenoisis has set in, the other lip 80 or 82 since it is loose, will continue to close until it reaches the stenoitic lip and thus there will be no leakage through valve 50. Also, if lips 80, 82 are not identical in any manner valve 50 will still properly close because of the overlap in lips 80, 82.

In the present valve even if there is shrinkage of the lips they are loose enough so that they will still close even with some shrinkage. In the case of prior art valves, shrinkage would cause the lips which are initially taut to retract so that they could not close at all. However, with the present valve this will not happen.

It is also important to note that because armature or base 60 is somewhat rigid it will tend to resist yielding under pressure. On the other hand, because the remainder of base ring 72 is soft and flexible it will readily yield under pressure. This feature is clearly shown in FIG. 7, wherein valve 50 is shown being flexed by a human hand. By the use of such a semi-flexible structure, valve 50 can be folded and manuvered so as to be readily inserted into the heart. This construction also enables valve 50 to respond more readily to movements of the heart once valve 50 has been installed.

Figure 9:
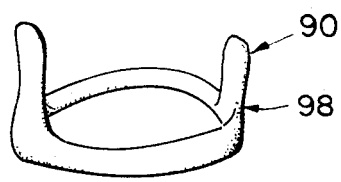
FIG. 9 shows the armature and struts of FIG. 8, covered with material to form an alternative support.

In FIGS. 8 and 9, there is shown an alternative support 90 formed upon a base 92 and struts 94, 96 fabricated as a continuous loop from a single wire or metal piece. Here again, the metal is of surgical grade and is preferably covered with plastic such as medical grade silicone. A thin covering of suitable soft biologically inert material 98 such as Dacron is then applied to form support 90. Thereafter a biological membrane (not shown) is applied to form the valve as hereinbefore described.

In FIGS. 10 and 11, an open base ring 100 is formed from relatively rigid wire or metal stock; and struts 102, 104, formed as inverted triangles are secured thereto as by welding, soldering, brazing or the like. It should be noted that strut 102 is higher then strut 104. Base 100 and struts 102, 104 are thereafter covered with soft fabric 110 to form a support 112 for a valve to be completed as hereinbefore described.

Figure 12:
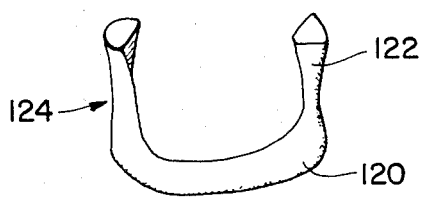
FIG. 12 shows yet another armature and struts construction.
Figure 13:
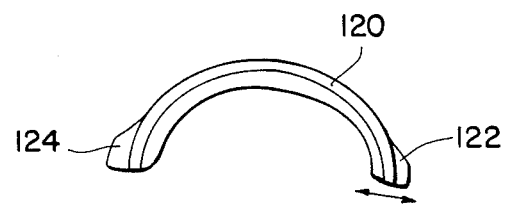
FIG. 13 shows a bottom view of the armature and struts of FIG. 12.

In the embodiment of FIGS. 12 and 13, a base 120 and struts 122, 124 are made integral and of stiff plastic material such as polypropylene. Base 120 is essentially semi-circular; while struts 122, 124 extend up and outwardly at an angle of 15–30 degrees from base 120.

Figure 16:
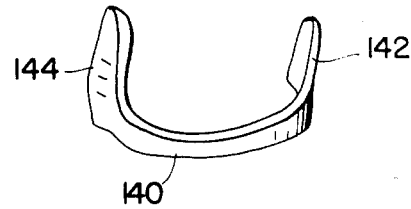
FIG. 16 shows yet still another alternative armature and struts construction.
Figure 17:
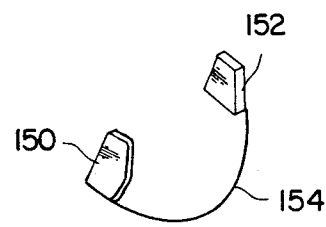
FIG. 17 shows yet still a further alternative armature and struts construction.

If more suitable, a base 140 (FIG. 16) with struts 142, 144 may be formed of plastic which is relatively flat. Or, alternatively a pair of struts 150, 152 (FIG. 17) may be interconnected by a wire or metal piece 154 to form a suitable base and struts.

Figure 14:
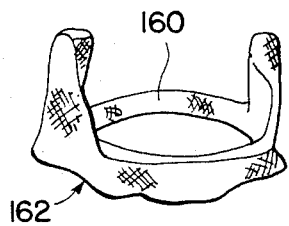
FIG. 14 shows the armature and struts of FIG. 13, covered with material to form yet another support.
Figure 15:
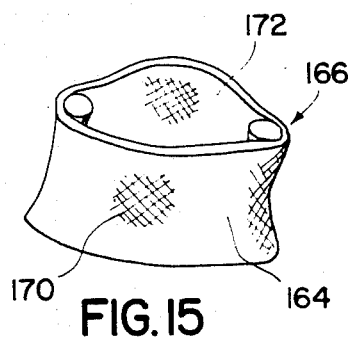
FIG. 15 shows a valve, using the support of FIG. 14, in open condition.

The base and strut structures of FIGS. 12, 13, 16 and 17 are thereafter covered with suitable soft fabric 160 (FIG. 14), as hereinbefore described, to form a support 162 upon which a biologically acceptable membrane 164 is applied as by sewing to fabric 162 to form a valve 166 all as described for the previously described embodiments. Here again, it should be noted that fabric 160 completes the base ring, and along with the rigid portion thereof, provides a base ring which is structurally sound enough to provide a secure attaching base while flexible enough to facilitate insertion and normal heart action. Membrane 164 is applied to provide lips 170, 172 which open fully (FIG. 15) to provide for unobstructed passage of blood and which, upon back pressure, close fully and with a substantial extent of mutual engagement so as to provide an effective closure.

Figure 18:
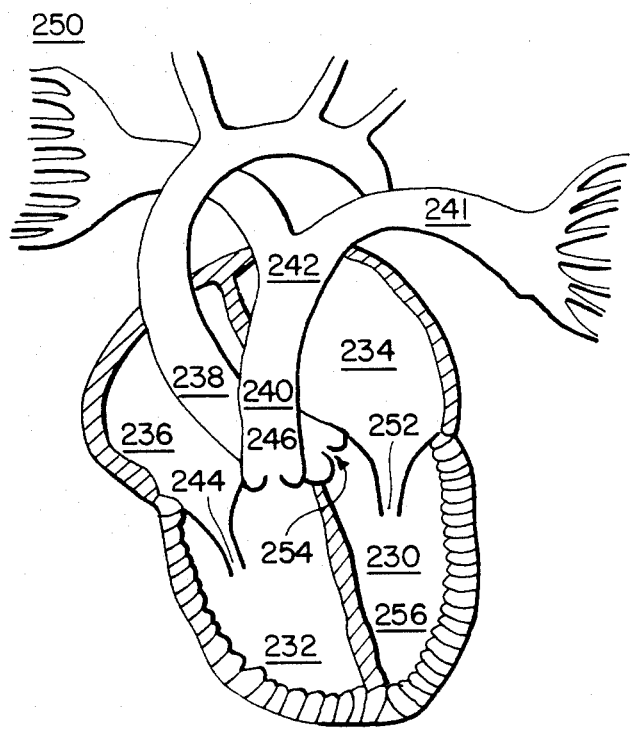
FIG. 18 is a schematic cross-sectional view of the human heart.

FIG. 18, is a schematic showing of a human heart illustrating the left ventricle 230, right ventricle 232, left auricle 234, right auricle 236, aorta 238 and pulmonary artery 240 including right and left pulmonary arteries 241 and 242. Normally blood flows through the heart from the veinous system into right auricle 236 through tricuspid valve 244 into right ventricle 232, and through pulmonic valve 246 and through right and left pulmonary arteries 241, 242 into lungs 250. From lungs 250 the blood comes back through left auricle 234 through mitral valve 252, the aortic valve 254 into aorta 238 and through the rest of the body. The two most important valves are mitral valve 252 and aortic valve 254. The basic reason for this is that left ventricle 230 is the basic pumping part of the heart. The walls 256 and 258 of left ventrical 230 are much thicker and more muscular than anywhere else in the heart. The pressures in left ventricle 238 range from 0–5 and 90–180 m.m. Hg, whereas in the other places in the heart, such as right ventricle 232, they only range between 0–5 and 2–30 m.m Hg. When blood flows from left auricle 234 to left ventricle 230 mitral valve 252 will open and aortic valve 254 will close. Then, left ventricle 230 contacts with mitral valve 252 closed and aortic valve 254 opens to cause blood to flow through aorta 238. If mitral valve 252 leaks oxygenated blood into left auricle 234, blood that should be flowing through aorta 238 will will not be and thus, there will be a substantial loss in the amount of oxygenated blood that reaches the rest of the body. In a similar manner, leakage through aortic valve 254 will cause an increase in the size of the heart muscle which will eventually lead to cardiac failure. Thus, even slight leakage in mitral valve 252 or aortic valve 254 will result in blood flowing the wrong direction through the heart, and would result in the eventual death of the person involved.

There are many reasons for failure of heart valves. Some of the most common are rheumatic diseases, such as rheumatic fever, congenital defects, such as birth defects.

In these diseases, the cusp of the valve will become stiff and either be permanently open or permanently closed and unable to properly function. Substantial leakage will occur which will eventually result in death. This leakage is often referred to as heart murmur being the sound of the backflow of the blood through the valve (flowing in the wrong direction).

Figure 20:
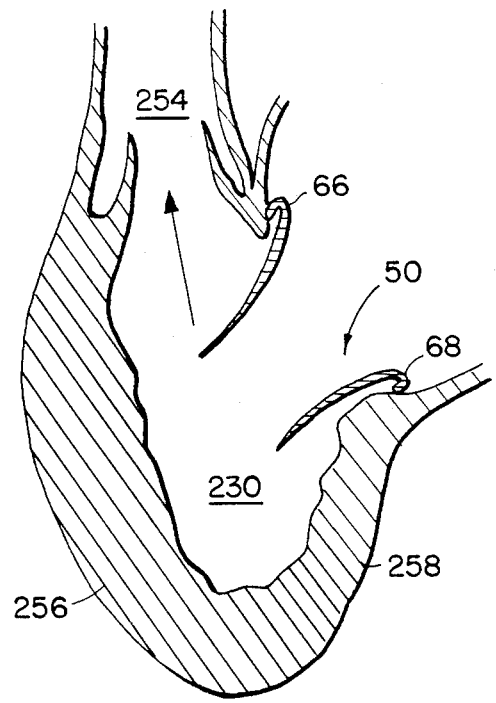
FIG. 20 is a schematic view of the left ventricle with a valve of this invention in place.
Figure 19:
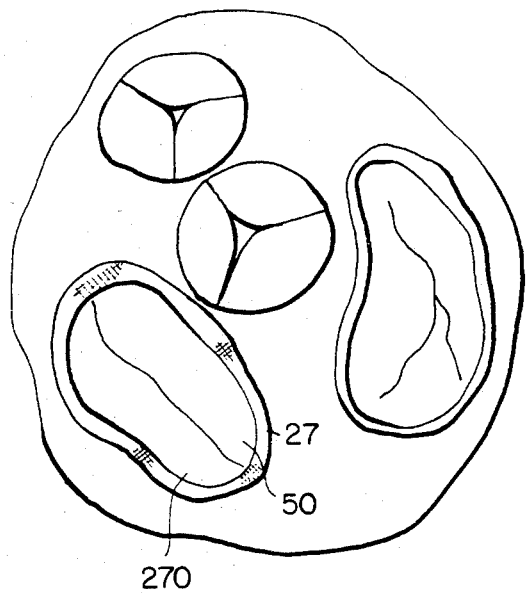
FIG. 19 is a schematic section view of a human heart with a valve of this invention being implanted.
Figure 21:
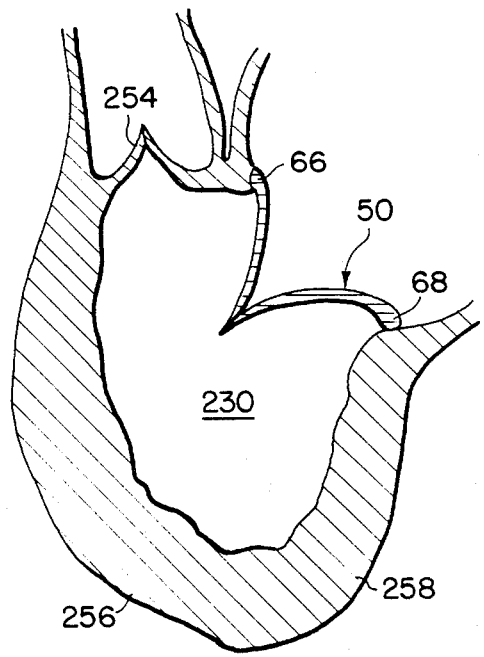
FIG. 21 is a view similar to that of FIG. 20 with the left ventricle in the contracting position.
Figure 22:
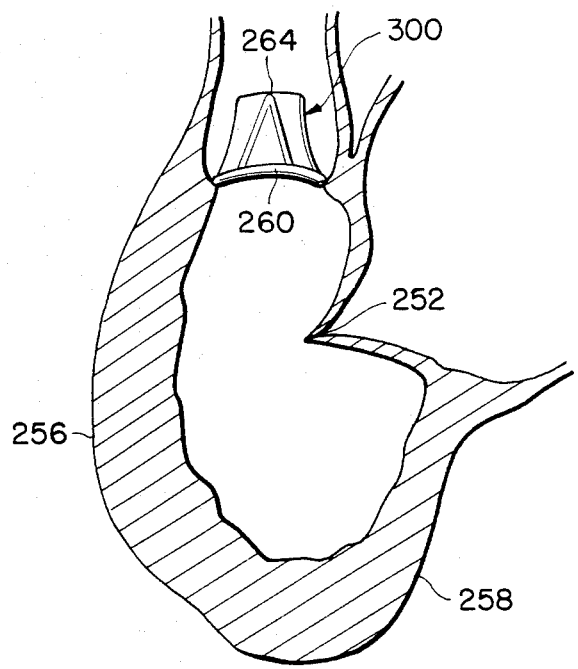
FIG. 22 is a schematic showing of the left ventricle with a valve in the aortic valve position.
Figure 23:
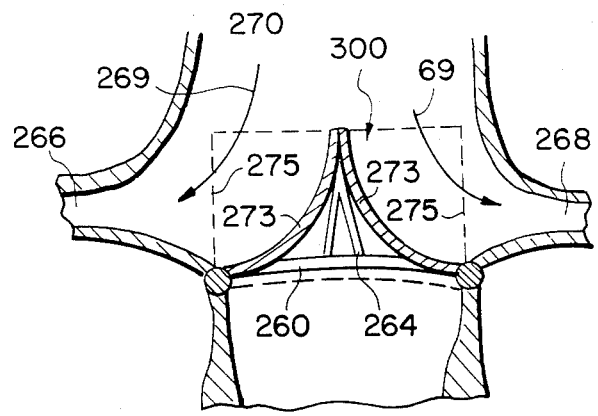
FIG. 23 is a more detailed showing of the valve implanted as in FIG. 22.

In replacing mitral valve 252, a valve as previously described (such as valve 50) is inserted in place of the defective mitral valve 252 (FIG. 18). Artificial valve 50 is sewn as at 270 (FIG. 19) into the heart by stitching the ring section of the material onto the remaining tissue around the circumference of the valve, once the defective natural valve has been removed. The resulting replacement is shown in FIGS. 19, 20 and 21 with valve 50 of this invention in position. It is located so that the shorter strut 66 is adjacent the aortic valve 254 and the longer strut 68 is positioned away from aorta 238. In this position, the ventrical can contract to the greatest extent without struts 66, 68 contacting the opposite wall of the heart. This is shown more clearly in FIG. 22. left ventricle 230 is shown in a somewhat contracted pumping position, with aortic valve 254 open and valve 50 of this invention closed. Also, since shorter strut 66 is adjacent the aortic opening, this will also permit normal flow through aorta 238. In FIGS. 22 and 23 a valve 300 (fabricated as a support 112 (FIG. 11) is in position in aorta 238 in replacement of the natural aortic valve 254. When it is placed in the heart it is positioned so that the struts 102, 104 are 90 degrees displaced on the coronary ostea 266 and 268 which are located in aorta 238. This is shown more clearly in FIG. 23. In this position, when valve 300 is closed the flow will be through the coronary ostea in the normal manner as shown by the arrow 269. When valve 300 is open the flow will be normal in the direction of arrow 271 with lips 273 of the valve moving into position of dotted line 275 to permit blood to flow through the valve. In this open position, lips 273 will block the entrance to the ostea in the same manner as a natural valve. It is noted that because of the flexibility of lips 273 the ability to completely open and close, valve 300 can be used in the aortic position where the prior art valves could not.

Figure 24:
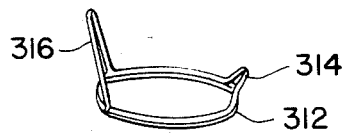
FIG. 24 shows still another alternative armature and strut construction.
Figure 25:
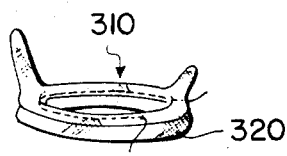
FIG. 25 shows the armature and struts of FIG. 24 covered with material to form yet another support.
Figure 26:
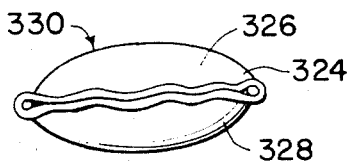
FIG. 26 shows a valve formed with the support of FIG. 25, and in its closed condition.

In the embodiment of FIGS. 24–26, there is shown a support 310 (FIG. 25) fabricated upon a base 312 (FIG. 24) formed from a ring of metal which takes the configuration of a complete oval. A pair of struts 314, 316 extend up from base 312. Suitable fabric 320 is applied over base 312 and struts 314, 316 and then a biological membrane 324 (of the type hereinbefore described) is applied over support 320 to form lips 326, 328 of valve 330.

Figure 27:
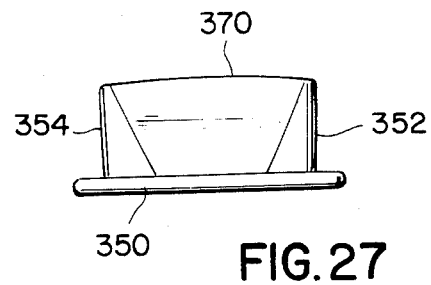
FIG. 27 shows another modified form of heart valve incorporating the instant invention.
Figure 28:
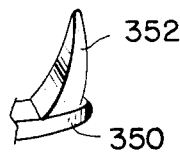
FIG. 28 shows one of the supporting struts of the valve of FIG. 27.
Figure 29:
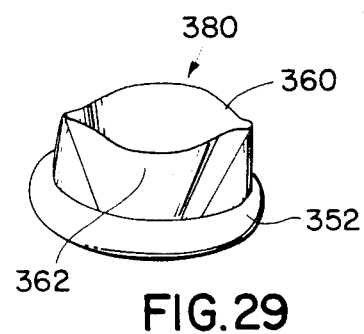
FIG. 29 is a perspective view of the heart valve of FIGS. 27 and 28 as shown in open condition.

In the embodiments of FIGS. 27–29, the ring 350 and the attached upwardly projecting substantially trapazoidal supporting struts 352 and 354 (FIG. 27) are all formed from flexible material. This can be any one of the many synthetic plastic like materials now available on the open market. Struts 352 and 354 are formed to have a tendency or bias in the outward direction from the ring 350.

Lips 360 and 362 are formed by securing a layer 370 of biologically acceptable inert material over a fabric tissue 372 of suitable synthetic material such as "Delrin" or "Teflon". By biologically acceptable is meant that, like the dura mater or pig or steer valve previously mentioned, the material is rendered inert, and will be acceptable within the human body, not rejected thereby. Materials such as silicone, "Silastic" and polyurethane have been found to be acceptable as such. In this valve, the struts and ring and biologically acceptable material can all be formed of the same material such as silicone, "Silastic" and polyurethane. The fabric tissue is added for strength, and, if desired, can be eliminated in this valve. When it is used to replace small valves since, then, the strength of the silicone, "Silastic" or polyurethane will be sufficient in itself.

In this embodiment, flexible ring 350 will offer no resistance to heart contractions, with less resulting trauma to the heart.

The outward bias of struts 352, 354 maintains, and, when valve 380 is in place in the heart, it helps to keep said lips closed.

Figure 30:
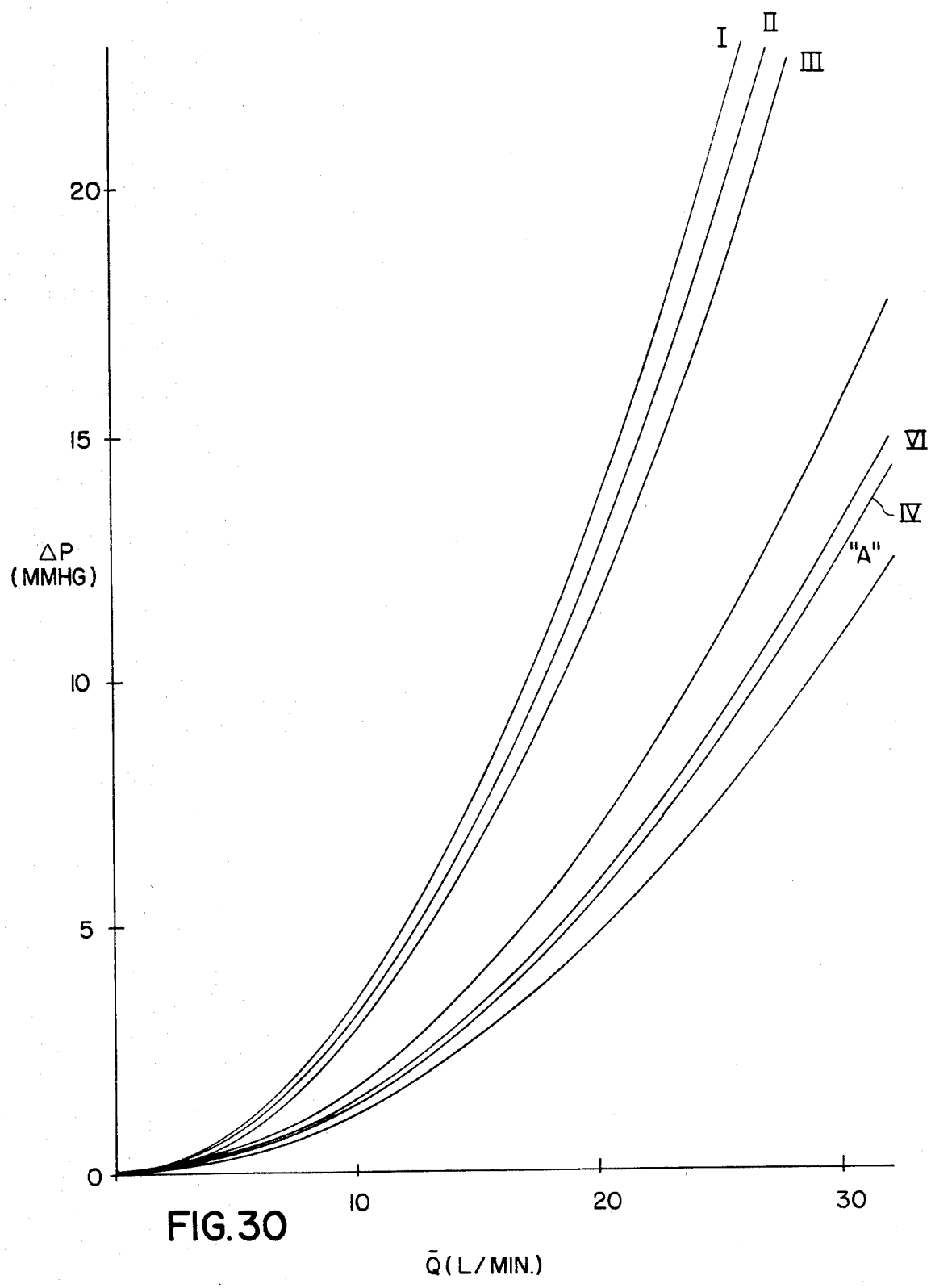
FIG. 30 and 31 are comparisons of $\Delta Pv$ the gradient (means $\Delta P$) vs. Flow (Q— Liters Per Minute) for prior art valves compared to a valve of the instant invention.
Figure 31:
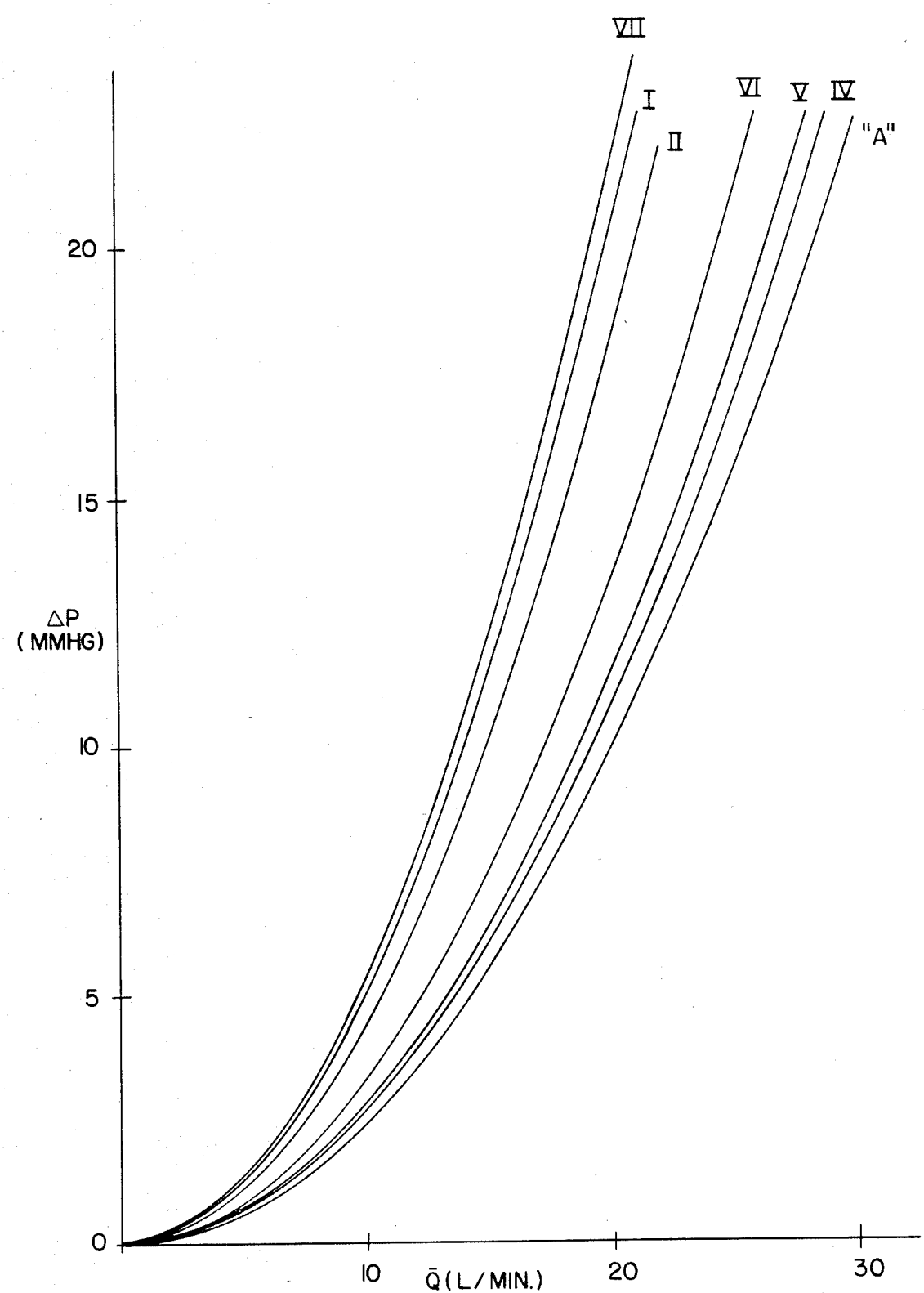

The graphs of FIGS. 30 and 31 show a comparison between a test valve fabricated in accordance with the instant invention and valves fabricated in accordance with prior art teachings. The graphs shows differential pressure ($\Delta P$) compared with test fluid flow in liters per minute. The lines are indicated as follows.

I—shows characteristics for a valve constructed as taught by Starr-Edwards and in U.S. Pat. No. 3,365,728;

II—shows characteristics of the Hancock Valve, and as shown in U.S. Pat. No. 3,570,014;

III—shows characteristics of the Beale Valve, and as shown in U.S. Pat. No. 3,491,376;

IV—shows characteristics of the Bjock-Shilley Valve;

V—shows the characteristics of Cutter-Cooley Valve;

VI—shows characteristics of the Ioniscu Valve;

VII—shows characteristics of the Kaster Valve, and as shown in U.S. Pat. No. 3,476,143; and A—shows characteristics of a valve constructed in accordance with the instant invention.

It should be noted that the most desirable characteristics are obtained by the valve constructed in accordance with the instant invention.

It will thus be appreciated that the same valve that is used for the mitral valve replacement can also be used for the tricuspid, and that the valve that is used for the aorta can be used for the pulmonic valve replacement. However, the aortic valve and mitral valve replacements are the most common and the most important.

While specific embodiments of the invention have been described, it will be appreciated that the invention is not limited thereto as many modifications thereof may be made by one skilled in the art which falls within the true spirit and scope of the invention. In addition, while I have shown the preferred forms of my invention it should be understood that such modifications may be made without depending from the spirit as comprehended by the following claims:

I claim:

1. A prosthetic heart valve, comprising:
 (a) a supporting structure comprising a base ring having two upwardly projecting and diverging struts, said base ring including a first ring portion which is formed from semirigid, flexible material and a second ring portion which is formed from soft flexible material;
 (b) a membrane forming lips which surround said base ring and struts to form a tubular opening with an exit end and an entrance end which are substantially of equal area; and
 (c) said lips being formed to close in an overlapping manner.

2. The valve of claim 1, wherein said struts extend from said first ring portion of said base ring.

3. The valve of claim 2, wherein said struts and said first ring portion are formed integral and from wire stock.

4. The valve of claim 3, wherein said wire stock is formed into circles at its ends which circles define the extremities of said struts.

5. The valve of claim 3, wherein said wire stock is folded back upon itself to define said struts and said first ring portion is a continuous loop of wire.

6. The valve of claim 2, wherein said struts and said first ring portion are formed integral and from plastic.

7. The valve of claim 6, wherein said struts and said first ring portion are formed from relatively thin plastic stock.

8. The valve of claim 2, wherein said struts are formed from plastic and are interconnected by said first ring portion formed from metal.

9. The valve of claim 1, wherein said second ring portion is formed from a fabric which also encases said struts and said first ring portion.

* * * * *